United States Patent [19]

Wennerberg

[11] Patent Number: 4,564,702

[45] Date of Patent: Jan. 14, 1986

[54] HYDROGENATION REACTIONS

[75] Inventor: Arnold N. Wennerberg, Chicago, Ill.

[73] Assignee: Standard Oil Company (Indiana), Chicago, Ill.

[21] Appl. No.: 489,407

[22] Filed: Apr. 28, 1983

[51] Int. Cl.$^4$ .............................................. C07C 63/04
[52] U.S. Cl. .................................... 562/493; 423/362; 585/277
[58] Field of Search .......................... 585/277; 562/493

[56] References Cited

U.S. PATENT DOCUMENTS

| | | | |
|---|---|---|---|
| 3,409,681 | 11/1968 | Kroll | 585/277 |
| 3,519,663 | 7/1970 | O'Brien et al. | 585/277 |
| 3,939,219 | 2/1976 | Wilkinson | 585/277 |
| 4,183,804 | 1/1980 | Antos | 585/277 |

FOREIGN PATENT DOCUMENTS 844243  8/1960  United Kingdom ................ 585/277

Primary Examiner—Paul J. Killos
Attorney, Agent, or Firm—James R. Henes; William T. McClain; William H. Magidson

[57] ABSTRACT

Catalytic reactions for the hydrogenation of alkenyl, alkynyl, aryl, cyano, imino, carbonyl and carboxyl groups and for the synthesis of ammonia are disclosed.

23 Claims, No Drawings

HYDROGENATION REACTIONS

BACKGROUND OF THE INVENTION

1. Field of the Invention

This invention relates generally to catalytic hydrogen transfer reactions involving the hydrogenation of alkenyl, alkynyl, aryl, cyano, imino, carbonyl and carboxyl groups and the synthesis of ammonia and more particularly concerns improvements in such reactions based upon the use of an improved metal-containing active carbon catalyst.

2. Description of the Prior Art

Catalytic hydrogen transfer reactions involving the hydrogenation of alkenyl, alkynyl, cyano, imino, aryl, carbonyl and carboxyl groups and the synthesis of ammonia occur in numerous refinery and chemical processing operations. It is highly desirable to maximize the selectivity and efficiency with which such hydrogen transfer reactions are performed.

It is known that the presence of metals in active carbon can greatly enhance the efficiency and selectivity of the active carbon when it is employed in catalytic, sorption, or filtering applications. However, attempts to incorporate metal compounds into activated carbon by conventional physical impregnation techniques have been problematical. One disadvantage with physical impregnation of activated carbon with metal compounds is that the small pores at the surface of the active carbon particles are inaccessible to liquid penetration and prevent penetration of the liquid, metal-containing impregnating solutions, thereby rendering impossible uniform and thorough impregnation of the carbon particles with metal. Furthermore, physical impregnation of the active carbon causes partial blocking of the pores of the carbon particles resulting in an appreciable reduction of the active surface area thereof. In addition, it is not possible to control to any large extent the total quantity of the metal applied to the active carbon particles by impregnation and its distribution on and in the carbon particles, with the end result that there is a substantial risk that the metal will crystallize and agglomerate in an undesirable manner on the carbon particles.

Several techniques have been proposed to overcome the problems associated with impregnating active carbon with metal compounds. For example, Dimitry, U.S. Pat. No. 3,886,093 discloses activated carbons having uniformly distributed active metal sites and a method for making such activated carbons. The method of Dimitry involves mixing an aqueous solution of a lignin salt with an aqueous solution of a transition metal salt to precipitate the transition metal and lignin as a metal lignate. The transition metal must be capable of forming a chemical bond with the lignin and in so doing precipitating the lignin from solution as a metal lignate. Dimitry discloses that the time required to complete the precipitation is less than one hour and that usually 30 minutes is sufficient for this purpose. According to Dimitry, suitably the wet metal lignate precipitate can then be dried in a spray drier. Dimitry states that, although drying the metal lignate precipitate is not critical to form an activated carbon product, drying is necessary to form a high surface area end product. However, Dimitry gives neither a general disclosure nor a specific example of what it means by a "high surface" area for its end product. Dimitry states that the active metal sites are uniformly distributed throughout the activated carbon end product and presents an electron micrograph of an activated carbon end product magnified 5,700 times. However, from this relatively low magnification micrograph, the distribution of the active metal sites in the activated carbon end product is not readily apparent.

Furthermore, Siren, U.S. Pat. No. 4,242,226 states that the metal content in the active carbon which can be achieved by pyrolysis and activation of a metal lignate precipitate is much too low for the majority of fields of use and that it is difficult using such technique to predetermine the properties of the resulting metal-containing active carbon end product owing to the substantially undefined structure of the lignin. Siren discloses an alternative technique in which a cation of calcium, magnesium, barium, aluminum, copper or a transition metal and an anionic group chemically bound to a polyhexose derivative are caused to react in solution, and the resulting product is precipitated either spontaneously or by adding a suitable precipitating agent. Siren discloses that, after separating the precipitate from solution, the precipitate can, if desired, be dried, for example, by spray drying. Thereafter the separated reaction product is pyrolyzed and activated to form the activated carbon. In the method of Siren, suitably the polyhexose derivative employed comprises an acid polyhexose derivative and preferably the anionic groups of the polyhexose derivative comprise carboxylic acid groups, sulfonic acid groups or phosphoric acid groups. Preferably the polyhexose derivatives contain from 1 to 3 metal cations per hexose unit.

Wennerberg et al., U.S. Pat. No. 4,082,694 disclose a process for making a high surface area active carbon by first heating an agitated combination of solid potassium hydroxide containing between 2 and 25 weight percent water and a carbonaceous material comprising coal coke, petroleum coke or a mixture thereof below about 483° C., then heating the resulting dehydrated product at a temperature between 705° C. and 983° C. to thereby form active carbon, and finally cooling the resulting activated product and removing essentially all of the inorganic material therefrom by water washing to form the high surface area active carbon end product. The resulting product is a high surface area active carbon material which has a cage-like structure exhibiting a microporosity which contributes to over 60 percent of its surface and which has an effective BET surface area of greater than about 2500 square meters per gram and a bulk density greater than about 0.25 gram per cubic centimeter. Wennerberg et al., U.S. Pat. Nos. 3,642,657 and 3,817,874 and Wennerberg, U.S. Pat. No. 3,726,808 disclose related methods for making high surface area active carbon products.

More recently, in my copending patent application Ser. No. 470,285 and copending patent application Ser. No. 470,487, both filed on Feb. 28, 1983, and both of which in their entirety are specifically incorporated herein by reference, I disclosed an active carbon composition comprising a substantially uniform dispersion of a metal or metal-containing material in a porous carbon matrix, wherein the weight ratio of the metal or metal-containing material to active carbon matrix is from about 1:10,000 to about 1:1, based on the weight of the metal or metal-containing material, respectively, and having a cage-like structure and a BET surface area of at least 800 square meters per gram and a bulk density of at least 0.1 gram per cubic centimeter, and two suitable methods for preparing such metal-containing active carbon compositions.

The preparation disclosed in my copending patent application Ser. No. 470,285 comprises the following steps: forming a uniform co-crystallite of a precursor of the metal or metal-containing material and of a carbon precursor, wherein the metal in the precursor of the metal or of the metal-containing material is a transition metal or a metal from Groups IIIA, IVA or VA of the Periodic Table of the Elements; forming a uniform powdered mixture of the co-crystallite and organic solids comprising an alkali metal hydroxide; pyrolizing the powdered mixture in an inert atmosphere at a temperature in the range of from about 400° C. to about 980° C. to form the carbon matrix having the metal or metal-containing material substantially uniformly dispersed therein; and separating unreacted inorganic material and inorganic reaction products other than the dispersed metal or metal-containing material from the porous carbon matrix to form the high surface area, porous carbon matrix end product.

The method disclosed in my copending application Ser. No. 470,487 comprises the following steps: forming a carbon precursor which contains the metal by the chemical reaction in solution of (1) a soluble carbon precursor having at least one anionic group chemically bound thereto and (2) a soluble cation of a transition metal or metal from Groups IIIA, IVA or VA of the Periodic Table of the Elements or a soluble cationic complex of such metal cation; precipitating and drying the metal-containing carbon precursor; forming a uniform powdered mixture of the metal-containing carbon precursor and inorganic solids comprising an alkali metal hydroxide; pyrolyzing the powdered mixture in an inert atmosphere at a temperature in the range of from about 400° C. to about 980° C. to form the carbon matrix having the metal or metal-containing material substantially uniformly dispersed therein; and separating unreacted inorganic material and inorganic reaction products, other than the dispersed metal or metal-containing material, from the carbon matrix to form the high surface area, porous carbon matrix end product.

SUMMARY OF THE INVENTION

The present invention pertains to improved hydrogen transfer reactions disclosed in part in Examples 15–20 of my aforesaid copending application Ser. No. 470,285 filed on Feb. 28, 1983. In one aspect, the present invention is a method for hydrogenating an alkenyl, alkynyl, aryl, cyano, imino, carbonyl or carboxyl group in one or more organic compounds, comprising: contacting one of the aforesaid compounds with hydrogen under hydrogenation conditions comprising a temperature in the range of from about ambient temperature to about 260° C. with an active carbon catalyst having a cage-like structure and a BET surface area of at least 800 square meters per gram and a bulk density of at least 0.1 gram per cubic centimeter and comprising a substantially uniform dispersion of a metal, metal-containing material, or both in a porous carbon matrix, wherein the dispersed metal and metal in the dispersed metal-containing material are each a transition metal and wherein the total concentration of dispersed metal and dispersed metal-containing material is from about 0.001 to about 30 weight percent calculated as the elemental metal and based on the weight of the catalyst.

The present invention is also a method for making ammonia comprising contacting nitrogen and hydrogen at a molar ratio of hydrogen-to-nitrogen of at least 3:1, at a temperature in the range of from about 150° C. to about 480° C. and at a pressure in the range of from about 6 to about 330 kilograms per square centimeter, with the catalyst employed in the aforesaid hydrogenation method of this invention.

DETAILED DESCRIPTION

The improved metal-containing active carbon catalyst employed in the method of this invention permits substantially improved selectivity and efficiency in hydrogen transfer reactions involving the hydrogenation of alkenyl, alkynyl, aryl, cyano, imino, carbonyl and carboxyl groups and the synthesis of ammonia. The extremely high selectivity and activity of the aforesaid metal-containing active carbon catalyst in such hydrogen transfer reactions result from the fact that the metal and metal-containing components thereof are substantially uniformly dispersed throughout the catalyst. In turn, in order to produce a catalyst having the aforesaid properties, it is critically important to employ one of the methods disclosed in my copending patent applications Ser. Nos. 470,285 and 470,487.

As employed in the preparation of the catalyst used in the method of the present invention, the method disclosed in my copending patent application Ser. No. 470,285 involves forming a uniform co-crystallite of a carbon precursor and of a precursor of the metal(s) and metal-containing material(s) to be dispersed.

Suitable carbon precursors for use in such method include aromatic carboxylic acids, phenols, aromatic amines and salts of any such materials. Preferably, metal salts of the aforesaid aromatic carboxylic acids and phenols are employed as the aforesaid carbon precursors.

The aforesaid aromatic acid may be any sulfur-free compound having an acid radical directly or indirectly attached to the benzene ring. Aromatic carboxylic acids are preferred and may be simple monocarboxylic acids, such as benzoic acid, or polycarboxylic acids, such as terephthalic, isophthalic, trimesic, and trimellitic, or polynuclear carboxylic acids, such as naphthoic acid, or polynuclear polycarboxylic acids, such as sulfur-free coke acids. It is also contemplated that the aromatic carboxylic acids may be derived from any suitable carbonaceous material which is subsequently oxidized to form the carboxylic acid. The feed material may be treated, when necessary or desired, to remove contaminants or undesirable elements. For example, sulfur-free petroleum coke has a metal content, but oxidation of petroleum coke with nitric acid serves the dual function of forming coke acid and removing metals. While sulfur-free petroleum coke acid having any degree of oxidation is suitable in the aforesaid catalyst preparation, the preferred sulfur-free petroleum coke acid is one having an elemental oxygen content of between about 20 to 30 weight percent.

Suitable precursors of the metal or metal-containing material for use in the formation of the co-crystallite in the catalyst preparation include salts or complexes of a transition metal and preferably of platinum, palladium, rhodium, molybdenum, chromium, tungsten, iron, cobalt, nickel or copper.

Any technique can be employed to form the co-crystallite which affords uniform co-crystallization—that is, simultaneous crystallization—of the carbon precursor and the precursor of the metal or metal-containing material and the formation of a substantially uniform co-crystallite thereof. Homogeneity of the co-crystallite mixture is essential to the ultimate formation of a uniform dispersion of the metal or metal-containing material in high surface area active carbon. A strongly preferred technique to form the uniform co-crystallite of the carbon precursor and precursor of the metal or metal-containing material involves the formation of a stable solution of both such precursors in a suitable solvent and spray drying such solution to dryness. In such technique, solvent removal must be carried out rapidly enough to maximize rapid, simultaneous and homogeneous co-crystallization of both precursors from solution. Spray drying provides the desired rapid evaporation to ensure rapid, simultaneous and uniform co-crystallization and formation of a homogeneous co-crystallite of both precursors.

In a spray drying system which is suitable for use in carrying out the spray drying step, a solution of the carbon precursor and of the precursor of the metal or metal-containing material is introduced into a drying chamber through a nozzle. An inert gas such as nitrogen or argon is introduced through a nozzle assembly to assist in atomizing the solution entering the drying chamber. A second larger volume of preheated gas, such as air or inert gas, depending upon requirements to prevent oxidation, is introduced into the drying chamber in a cocurrent or countercurrent manner. This preheated gas treatment provides the necessary high vapor capacity to effect rapid evaporation of the solvent from the atomized droplets. The resulting dry co-crystallite powder is entrained in the drying gas stream and separated from the gas stream in a sequence of appropriate cyclones. Effective solid-gas separation may be accomplished by two appropriate cyclones in series. Water vapor-laden gas is usually discharged in the atmosphere, and co-crystallite powder passes downward in and from the cyclones for collection.

In the spray drying technique, it is of course essential that stable solutions of the carbon precursor and precursor of the metal or metal-containing material be employed. Although it is preferred that a single solution containing dissolved carbon precursor and precursor of the metal or metal-containing material be employed, it is also suitable to employ separate solutions, with one containing the dissolved carbon precursor and the other containing the dissolved precursor of the metal or metal-containing material. When two such solutions are employed, the two solutions are mixed upstream of the aforementioned nozzle and aspirated together into the aforementioned drying chamber. Although any convenient solvent can be employed, water is the preferred solvent.

In the spray drying technique, forms of each of the carbon precursor and of the precursor of the metal or metal-containing material which are both soluble in the solvent used, or each soluble in one or the other of the solvents used, must be employed. Variables which can be controlled to effect the necessary solubility of both precursors in the same solvent or of each precursor in a different solvent include the pH of the solvents, the concentration of the precursors in the solvents, and the forms in which the precursors are introduced into the solvents—for example, the identity of the salt or complex of the precursor of the metal or metal-containing material. Water soluble forms of the carbon precursor include potassium, sodium, rubidium and ammonium salts of aromatic carboxylic acids and phenols in an alkaline aqueous solution and aromatic amine hydrochlorides in an acidic aqueous solution.

Table 1 contains a list of merely a few illustrative examples of water-soluble metal salts and complexes which serve as precursors of metals and metal-containing materials in the method of this invention.

TABLE 1

| Precursor | Metal or Metal-Containing Material |
|---|---|
| $K_2Cr_2O_7$ | $Cr_2O_3$ |
| $KMnO_4$ | $MnO_2$ |
| $Na_2WO_4$; $(NH_4)_2WO_4$ | $W_2O_3$ |
| $K_2MoO_4$; $(NH_4)_2MoO_4$ | $MoO_2$ |
| $Co(NH_3)_4Cl_2$, Cobalt phenolate complex | CoO, Co |
| $Cu(NH_3)_4Cl\ 2$ | CuO, Cu |
| $Ni(NH_3)_4Cl_2$ | NiO, Ni |
| $Ag(NH_3)_2Cl$ | $Ag_2O$, Ag |
| Ferric phenolate complex | $Fe_2O_3$, Fe |
| $RhCl_3$ complexes with glycine or EDTA | RhO 2, Rh |
| $PdCl_2$ complexes with glycine, EDTA or hydroxquinoline | PdO, Pd |
| $H_2PtCl_6$ complexes with glycine, EDTA or $NH_3$ | PtO, Pt |

In the alternative, as employed in the preparation of the catalyst used in the method of this invention, the method disclosed in my copending patent application Ser. No. 470,487 involves forming in solution a precipitate of a carbon precursor containing a precursor of the metal or metal-containing material. In such case, the metal-containing carbon precursor is formed by a chemical reaction involving a cation of the aforesaid metal or a cationic complex of such metal cation with an anionic group on one of the aforementioned suitable carbon precursors, wherein both the carbon precursor and the metal cation or cationic complex of the metal ion are soluble in the solvent employed for this reaction. Since water is the preferred solvent, water-soluble metal cations or water-soluble cationic complexes of the metal ion are preferred for use in the method of this invention. It is of course a critical requirement of the method of this invention that the metal cation or the cationic complex of the metal ion reacts with the carbon precursor so as to form a chemical bond with at least one anionic group on the carbon precursor.

In such technique, the carbon precursor and metal cation or cationic complex of the metal ion are combined in the solvent employed and in the proportions necessary to achieve the desired concentration of metal or metal-containing material in the final product. Chemical reaction between the carbon precursor and the metal cation or cationic complex of the metal ion either occurs spontaneously or is induced by adjustment of any convenient solution parameter, for example, the temperature or pH. Depending upon the particular carbon precursor used and the particular metal cation or cationic complex of the metal ion used, the reaction product thereof either precipitates out spontaneously or is precipitated by addition of a suitable precipitating agent or by adjustment of the temperature or pH of the solution, or is dired to the desired dry substance content. The resulting precipitated reaction product is then separated from solution by filtration, centrifugation or the like, and if desired, washed to remove any excess metal salt solution. The separated precipitate is then dried.

The co-crystallite powder or the dried precipitate formed as described above is then intimately mixed with the inorganic solids comprising an alkali metal hydroxide. Preferably at least 25 weight percent of the inorganic solids is the alkali metal hydroxide. Although not intending to limit the scope of the present invention by any theoretical explanation, the role of the alkali metal hydroxide in the formation of the active carbon of the present invention is believed to occur by reaction with the carbon precursor during pyrolysis to thereby propagate the formation of active carbon. The particle size of the inorganic solids need only be sufficiently small to ensure that the inorganic solids disperse well enough in the aforesaid co-crystallite powder or dried precipitate that an intimate mixture is formed. The weight ratio of alkali metal hydroxide-to-co-crystallite or -to-dried precipitate in the resulting mixture is from about 1:1 to about 5:1, preferably from about 2:1 to about 4:1 and more preferably from about 2.5:1 to about 3.5:1.

Although a hydroxide of any metal of Group IA of the Periodic Table can be mixed with the co-crystallite or dried precipitate in the method of this invention, potassium hydroxide is strongly preferred. In addition to its ready availability and relative low cost, potassium hydroxide is advantageous because unless potassium hydroxide is employed, it is extremely difficult to obtain a metal-containing active carbon end product having a surface area of at least 1,000 square meters per gram, without additional treatment being required. Furthermore, as will be discussed hereinbelow, potassium hydroxide is preferred because it is highly soluble in water and its carboxylate salts are highly soluble in water.

Preferably the alkali-metal hydroxide is hydrated. The water of hydration serves to assist in lowering the fusion temperature of the alkali metal hydroxide and in producing a uniform melt of the co-crystallite or dried precipitate and alkali metal hydroxide in the pyrolysis step before pyrolysis occurs, to thereby facilitate mixing of the alkali metal hydroxide and co-crystallite or dried precipitate before reaction occurs. Preferably the alkali metal hydroxide contains from 2 to 25 weight percent of water of hydration.

The inorganic solids can comprise, in addition to the alkali metal hydroxide, an alkali metal salt such as an alkali metal halide, carbonate, sulfate, phosphate, nitrate or oxide. Preferably potassium is the alkali metal in the alkali metal halide, carbonate, sulfate, phosphate, nitrate or oxide. In one variation, some or all of the alkali metal salt is mixed with the carbon precursor and precursor of the metal or metal-containing material prior to or during formation of the co-crystallite, for example, in the spray drying step.

The intimate mixture of co-crystallite powder or dried precipitate and inorganic solids is then pyrolyzed under an inert atmosphere such as nitrogen gas. The pyrolysis temperature is selected to be high enough to decompose the carbon precursor and less than the graphitization temperature of carbon, that is, from about 400° C. to about 980° C., preferably from about 700° C. to about 900° C. The rate of temperature increase to which the mixture of co-crystallite or dried precipitate and inorganic solids is subjected in the pyrolysis chamber is preferably at least 35° C. per minute and more preferably at least 300° C. per minute. Such rates of temperature increase of at least several hundred degrees centigrade per minute are readily attainable with microwave heating. Higher rates at which the temperature of the mixture is raised from ambient temperature of the final pyrolysis temperature effectively neutralize the tendency toward the formation of separate phases as a result of differences in the temperatures and rates at which the carbon precursor and precursor of the metal or metal-containing material pyrolyze. Such phase separation is manifested by relatively larger crystal growth for the metal or metal-containing material dispersed in the active carbon end product and thus is detectable by a relative increase in the crystallite size and by relative decreases in the uniformity of dispersion of the metal or metal-containing material and of the accessible surface area of the dispersed metal or metal-containing material.

Following the pyrolysis step, while still under a blanket of inert gas, the pyrolysis chamber and its contents are cooled and the powdered pyrolysis product is suspended in a suitable liquid, preferably water, in the blanketed pyrolysis chamber and then transferred as a slurry to a receiver. The solvency of the slurry liquid must be controlled to ensure that the dispersed metal or metal-containing material does not dissolve in the slurry liquid. For example, when substantially neutral water is employed as the slurry liquid, the resulting slurry of the powdered pyrolysis product is alkaline and has a pH of about 12. Under these conditions, if the metal dispersed in the active carbon is in the form of an amphoteric metal oxide, the metal oxide would dissolve in the water and would thereby be removed from the active carbon. For example, dispersed $WO_3$, $MoO_3$ and $V_2O_3$ would dissolve as $K_2WO_4$, $K_2MoO_4$ and $KVO_3$, respectively. Since it is necessary to prevent solubilization of the dispersed metal oxide in such cases, before the powdered pyrolysis product is rinsed or slurried, the pH would have to be adjusted with a suitable acid solution such as acetic acid, or vapor such as carbon dioxide or acetic acid vapor, so that the resulting water slurry would have a pH of about 7.0–8.0.

The slurry is then filtered to separate the powdered pyrolysis product from the slurry liquid. Thereafter the powdered product is purified by repeated washings with a suitable solvent, preferably water, to remove the alkali metal therefrom and yet to leave undissolved the dispersed metal or metal-containing material in solid form in the active carbon matrix. When water is used as the wash solvent and when the dispersed metal is in the form of an amphoteric metal oxide, before the powdered pyrolysis product is washed, the pH of the water should be from 7 to 8 to ensure dissolution of the alkali metal in the water but to prevent dissolution of the dispersed metal oxide. Since potassium salts are more soluble than the corresponding salts of the other alkali metals, it is highly preferred that potassium is the alkali metal in the alkali metal hydroxide, in the dried precipitate and in any alkali metal salt mixed with the co-crystallite prior to the pyrolysis step to facilitate removal thereof from the active carbon end product.

Thereafter the powdered product is dried using any conventional and suitable drying technique.

The active carbon catalyst employed in the instant invention has a cage-like structure which contributes preferably to over sixty percent of its surface and, more preferably, to over 80 percent of its surface and, most preferably, to over 90 percent of the carbon surface, as measured by phase contrast, high resolution electron microscopy. This cage-like structure is characterized in that the individual cages are of a size to exhibit properties of microporosity, that is, essentially complete filling of the individual cages by the adsorbate at low effective concentration to give a large micropore volume. The cages in the cage-like structure are substantially homogeneous in size and the individual cages are clearly evident and appear to be formed using single sheets of graphitic-type lamellae. This cage-like structure is responsible for the multi-layer adsorption demonstrated by the active carbon catalysts employed in this invention and the extremely large effective surface areas as measured by the BET method.

The active carbon catalyst produced preferably has an effective BET surface area greater than about 800 square meters per gram, more preferably, greater than about 1,600 square meters per gram, and, most preferably, greater than about 2,000 square meters per gram. The active carbon catalyst preferably has a bulk density which is preferably greater than about 0.1 gram per cubic centimeter and, more preferably, greater than about 0.2 gram per cubic centimeter.

Any transition metal or any combination of transition metals or a material containing any such metal or combination can be dispersed in the active carbon matrix in the catalyst employed in the present invention. Preferably the dispersed metal and the metal in the dispersed metal-containing material are platinum, palladium, rhodium, molybdenum, chromium, tungsten, iron, cobalt, nickel or copper. Preferably the dispersed metal-containing material is a metal oxide. The dispersed metal(s) and metal-containing material(s) are at a total concentration level of from about 0.001 to about 30 weight percent, preferably from about 0.1 to about 20 weight percent, calculated as the elemental metal(s) and based on the weight of the catalyst.

Although the crystallite size of the dispersed metal or metal-containing material depends on the metal, the form in which it is dispersed, and the rate of increase of temperature to which the mixture of co-crystallite powder or dried precipitate and inorganic solid are subjected during the pyrolysis step of the method of this invention, the average crystallite size of the dispersed metal or metal-containing material is generally in the range of from about 5 Å to about 30 Å of the dispersed metal or molecules of the dispersed metal-containing material. For example, when a precursor of platinum is employed in the method of this invention, and when the rate of temperature increase in the pyrolysis step is at least 35° C. per minute, the platinum is dispersed in the end product predominantly as platinum metal having an average crystallite size equivalent to from 5 Å to 15 Å of platinum metal.

The metal-containing active carbon catalysts employed in the method of the present invention possess substantially improved resistance to thermally or chemically induced sintering or recrystallization of the dispersed metal or metal-containing material to form a dispersed material of relatively larger crystallite size and relatively lower effective surface area. Upon exposure to high temperatures, for example, 900°-1150° C. for 12 hours, or to certain chemical treatments, for example, with 106 percent phosphoric acid for 65 hours at 200° C., the crystals of dispersed metal or metal-containing material recyrstallize to form larger crystals. However, this tendency to such crystal growth is much less than for prior art metal-containing carbon catalysts and can be minimized by the use of higher rates of increasing the temperature in the pyrolysis step.

The dried metal-containing active carbon catalyst generally has an average particle size in the range of from about 25 to about 28 microns and in that size range is suitable for use in many applications. However, in certain applications such as for use in a packed or fluidized bed, it may be desirable or necessary to employ larger particles.

A suitable, low-cost granular activated carbon having a high surface area and a suitable particulate form with sufficient crush strength and abrasion resistance comprises a clay binder which is capable of forming a high viscosity gel when dispersed in water, for example, the montmorillonite clays. When using activated carbon, the montmorillonites enable the carbon to retain a high percentage of its effective surface area. In fact, the loss of effective surface area due to the presence of the clay binder is only about equal to the relative percentage of clay binder present. Hence, for a granular activated carbon containing 15 weight percent montmorillonite, the effective surface area would be only about 15 percent less than the effective surface area of the powdered activated carbon used as the starting material. The aforesaid granular activated carbon containing clay binder may be prepared in any size or shape desired. A characteristic of the granular activated carbon containing montmorillonite clay binder is that it retains throughout the fabricated form the average pore size of the powdered carbon starting material. Such granular activated carbons are also characterized by a good high temperature strength and crush strength. The weight ratio of activated carbon to clay binder in such granular activated carbon is from about 90:10 to about 70:30, on a dry basis.

A suitable process for preparing the aforesaid granular activated carbon comprises the steps of: (a) blending the activated carbon with a powdered montmorillonite clay binder in the presence of sufficient water to achieve a composition having from about 30 to about 40 weight percent solids and a carbon:binder weight ratio of from about 90:10 to about 70:30; (b) compounding the composition to achieve dispersion of the clay binder in the aqueous phase and penetration of the resulting aqueous-binder phase into the interstitial spaces between the activated carbon particles; (c) extruding the composition through an orifice to form an extrudate; (d) drying the extrudate at a maximum temperature of about 191° C. in a manner so as to minimize the shock effects of rapid water evaporation from the porous carbon and secondary carbon surface oxidation by water vapor; and (e) curing the extrudate at a temperature sufficient to effect a physical-chemical change in the extrudate which is manifested by increased hardness and stability.

Suitable curing temperatures are from about 774° C. to about 1038° C., preferably in the range from about 899° C. to about 927° C.

Drying is preferably accomplished by a gradual increase in temperature to minimize the effects of water evaporation on the strength of the carbon structure. A time-temperature profile which has been found effective comprises air drying the extrudate material at increasing temperatures wherein the temperature is increased at a rate of about 2.8° C. per minute until a drying temperature of 94° C. is reached. Thereafter the temperature is increased at a rate of 5.5° C. per minute until a maximum drying temperature of 191° C. is reached. Total drying time is from about 45 minutes to about 1 hour. The resulting water content is about 2 weight percent.

In the alternative, the metal-containing active carbon catalyst can be granulated with alumina using the procedure exemplified in Example 9 hereinbelow.

It may also be desirable in certain instances to reduce the particle size of the metal-containing active carbon catalyst employed in the method of this invention below the aforesaid average particle size of 25–28 microns. In such cases, the metal-containing active carbon catalyst employed in the method of this invention can be milled by any convenient method to small particle sizes. A major advantage of the uniform distribution of metal or metal-containing material in the active carbon catalyst is that reduction of the particle size by milling or attrition does not affect the distribution of the dispersed metal component within the active carbon or on its exterior surface and hence of the availability or accessibility of the dispersed metal component.

Suitable groups for hydrogenation by the method of this invention include alkenyl, alkynyl, aryl, cyano, imino, carboxyl and carbonyl groups. The alkenyl and alkynyl groups can be present in acyclic or cyclic aliphatic compounds, for example, propylene and cyclohexene. The carboxyl group can be present as a carboxylic acid functional group or the ester, amide, imide or anhydride derivative thereof. The carbonyl group can be present as an aldehyde or ketone functional group. The degree of saturation of the aforesaid groups with hydrogen by the method of the present invention of course depends on the molar ratio of hydrogen-to-the organic compound and other reaction conditions employed. For example, under appropriate conditions, terephthalic acid is reduced to p-carboxybenzaldehyde, and in turn p-carboxybenzaldehyde is reduced to p-toluic acid.

Suitable conditions for hydrogenation by the method of this invention include a temperature in the range of from about ambient temperature to about 260° C., preferably at least about 40° C., a hydrogen partial pressure in the range of from about 2 to about 75 kilograms per square centimeter, and a total pressure in the range of from about 4 to about 75 kilograms per square centimeter. In addition, a total space velocity in the range of from about 0.01 to about 10, preferably from about 0.1 to about 8, grams of organic compound(s) containing the functional group(s) to be hydrogenated per gram of catalyst per hour is typically employed.

Suitable conditions for the synthesis of ammonia by the method of this invention include a temperature in the range of from about 150° C. to about 480° C., a molar ratio of hydrogen-to-nitrogen of at least 3, a nitrogen partial pressure of from about 1.5 to about 82 kilograms per square centimeter, a hydrogen partial pressure of from about 4.5 to about 248 kilograms per square centimeter, and a total pressure in the range of from about 6 to about 330 kilograms per square centimeter. In addition, a space velocity in the range of from about 500 to about 100,000 volumes of nitrogen and hydrogen combined per volume of catalyst per hour is typically employed.

While the invention is described in connection with the specific examples below, it is to be understood that these are for illustrative purposes only. Many alternatives, modifications and variations will be apparent to those skilled in the art in light of the examples below and such alternatives, modifications and variations fall within the scope and spirit of the appended claims.

EXAMPLE 1

6.53 grams of chloroplatinic acid ($H_2PtCl_6 \cdot 6H_2O$) were introduced into 1100 grams of water, and 6 grams of ethylenediamine tetraacetic acid (EDTA) were introduced to 100 grams of water. Sufficient amounts of a dilute solution of ammonium hydroxide were added to the aqueous solution of EDTA as necessary to raise the pH of the solution to 8 and to thereby form a stable solution of the ammonium salt of EDTA. When the solutions of chloroplatinic acid and of the EDTA salt were combined, a stable solution of the complex of the chloroplatinate anion with the ammonium salt of EDTA was formed.

166 grams of terephthalic acid were introduced to 2200 grams of water and dissolved therein as ammonium terephthalate by the addition of sufficient amounts of a concentrated solution of ammonium hydroxide to raise the pH of the resulting solution to 8.0–8.5. The solutions of the complex of the chloroplatinate salt with the EDTA salt and of the terephthalate salt were then combined to form a stable homogeneous solution at 21°–29° C. The combined solution was then spray dried using the procedure described above with respect to FIG. 1 to yield finely divided co-crystallite powder of potassium terephthalate and potassium chloroplatinate.

20 grams of the co-crystallite powder were then dry blended with 54.06 grams of 90 percent potassium hydroxide powder and 59.89 grams of potassium carbonate powder in a Waring blender to produce 134 grams of a uniform powdered mixture. This entire powdered mixture was transferred to a rotating quartz calcining tube equipped for continuous argon purge, placed in a tubular furnace, and preheated to 650° C. The temperature of the powdered mixture rose at a rate of 66.7° C. per minute to 650° C. The quartz tube remained in the furnace during its heat up and during the one hour period at 650° C., during which time the powdered mixture pyrolized to form a powdered pyrolysis product and after which time the tube was withdrawn from the furnace and allowed to cool to ambient temperature. The quartz tube and its contents were maintained under a blanket of argon throughout the period before introduction of the powdered mixture into the quartz tube, during the pyrolysis and during cool down of the quartz tube and its contents to ambient temperature. While still under an argon blanket, the cooled pyrolysis product was rinsed with water from the cooled quartz tube. After separation from the water, the pyrolysis product was repeatedly washed with water to remove the potassium salts therefrom, until a resulting wash water had a pH of 7. A final wash with a solution of 1 weight percent of acetic acid in water was performed to remove the last traces of potassium salts from the pyrolysis product. The resulting washed pyrolysis product was dried in a vacuum oven at 105° C. under a nitrogen blanket.

The resulting dried pyrolysis product weighed 6.0 grams, had a BET surface area of 2744 square meters per gram and contained 3.66 percent of platinum by weight, based on the weight of the pyrolysis product. Electron micrographs of the dried pyrolysis product are shown in FIGS. 1 and 2. The platinum was predominantly in the form of elemental platinum. The platinum had a surface area of 11.0 square meters per gram as determined by CO chemisorption, and 99.03 percent of the platinum had an average crystallite size less than 35 Å, as determined by X-ray diffraction.

Thermal sintering of the powdered pyrolysis product at 1021°–1150° C. for a period of 12 hours resulted in recrystallization of a portion of the dispersed platinum as manifested by crystal growth of 26 weight percent of the dispersed platinum to an average crystallite size of about 105 Å. An electron micrograph of the sintered pyrolysis product is shown in FIG. 3. In addition, contacting of the powdered pyrolysis product with 106 percent phosphoric acid for 65 hours at 200° C. resulted in recrystallization of the dispersed platinum as manifested by crystal growth of 30 weight percent of the dispersed platinum to an average crystallite size of 60 Å.

EXAMPLE 2

The procedure of Example 1 was repeated, with the difference of inserting the powdered mixture of co-crystallite, potassium hydroxide and potassium carbonate into the purged quartz tube at ambient temperature and then inserting the tube into the furnace. The temperature of the tube's contents rose at a rate of 11.1° C. per minute, instead of 66.7° C. per minute, from ambient temperature to 650° C.

The resulting dried pyrolysis product weighed 6.0 grams, had a BET surface area of 2164 square meters per gram and contained 3.97 percent of platinum by weight, based upon the weight of the pyrolysis product. An electron micrograph of the dried pyrolysis product is shown in FIG. 4. The platinum was predominantly in the form of elemental platinum. The platinum had a surface area of 9.0 square meters per gram as determined by CO chemisorption, and 83.87 percent of the platinum had an average crystallite size less than 35 Å, as determined by X-ray diffraction.

Thermal sintering of the powdered pyrolysis product at 1021°–1150° C. for a period of 12 hours resulted in recrystallization of the dispersed platinum as manifested by crystal growth of 100 percent of the dispersed platinum to an average crystallite size of 135 Å. In addition, treatment of the powdered pyrolysis product with 106 percent phosphoric acid for 65 hours at 200° C. resulted in recrystallization of the dispersed platinum as manifested by crystal growth of 98 percent of the dispersed platinum to an average crystallite size of 60 Å.

EXAMPLE 3

The procedure of Example 1 was repeated with the following exceptions. Instead of concentrated ammonium hydroxide, 120 grams of potassium hydroxide were added to the terephthalic acid solution to solubilize the terephthalic acid as potassium terephthalate. Instead of the solution containing chloroplatinic acid, a stable solution of a complex of the palladium cation with the potassium salt of EDTA was formed by introducing 0.832 gram of palladium chloride (in the form of $H_2PdCl_4$) into 150 grams of water containing the potassium salt of EDTA formed by neutralizing 20 grams of EDTA to a pH of 8.0 with an aqueous solution of potassium hydroxide. Instead of introducing the powdered mixture of co-crystallite, potassium hydroxide and potassium carbonate into the purged quartz tube at 650° C., the tube was at ambient temperature as in Example 2, and the temperature of the tube's contents rose at a rate of 11.1° C. per minute from ambient temperature to 650° C.

The resulting dried pyrolysis product weighed 3.4 grams, had a BET surface area of 3433 square meters per gram, and contained 1.00 percent of palladium by weight, based on the weight of the pyrolysis product. The palladium was predominantly in the form of elemental palladium. The dispersed palladium had a surface area of 0.65 square meters per gram, as determined by CO chemisorption, and 82 percent (0.82 weight percent based on the weight of the pyrolysis product) of the palladium had an average crystallite size less than 35 Å. Thermal sintering of the pyrolysis product at 1021° C. for a period of 12 hours resulted in recrystallization of the palladium as manifested by crystal growth of 100 percent of the dispersed palladium to an average crystallite size of 118 Å.

EXAMPLE 4

The procedure of Example 1 was repeated with the following exceptions. An aqueous solution of potassium terephthalate formed as in Example 3 was used in place of the ammonium terephthalate solution formed as in Example 1. Instead of the solution of the complex of the chloroplatinate anion employed in Example 1, a stable aqueous solution of $Ni(NH_3)_4(acetate)_2$ was formed by neutralizing 11.09 grams of $Ni(acetate)_2.4H_2O$ with ammonium hydroxide in 150 milliliters of water. The resulting dried pyrolysis product weighed 6.0 grams, had a BET surface area of 2085 square meters per gram, and contained 1.21 percent of nickel by weight, based on the weight of the pyrolysis product. The nickel was predominantly in the form of elemental nickel. 76 weight percent of the dispersed nickel had a crystallite size less than 35 Å.

EXAMPLE 5

The procedure of Example 4 was repeated, with the difference of inserting the powdered mixture of co-crystallite, potassium hydroxide and potassium carbonate into the purged quartz tube at ambient temperature and then inserting the tube into the furnace. The temperature of the tube's contents rose at a rate of 11° C. per minute instead of 66.7° C. per minute. The resulting dried pyrolysis product weighed 6.0 grams, had a BET surface area of 2445 square meters per gram, and contained 1.3 percent of nickel by weight, based on the weight of the pyrolysis product. The nickel was predominantly in the form of elemental nickel. 22 percent of the dispersed nickel had a crystallite size of less than 35 Å.

EXAMPLE 6

0.65 gram of chloroplatinic acid ($H_2PtCl_6.6H_2O$) was dissolved in 250 grams of water and 0.627 gram of rhodium chloride ($RhCl_3.3H_2O$) was dissolved in 250 grams of water, and the two solutions were combined. To this solution was then added a solution of 3 grams of glycine in 100 grams of water neutralized to a pH of 8 with potassium hydroxide, to form stable complexes of glycine with the chloroplatinate anion and the rhodium cation. 166 grams of terephthalic acid were introduced into 2200 grams of water and dissolved therein as potassium terephthalate by the addition thereto of 75 grams of 90 percent potassium hydroxide and then the adjustment of the pH to 8. The solution of the glycine complexes and of potassium terephthalate was then combined to form a stable homogeneous solution at 21°–29° C. The combined solution was then spray dried to yield 222 grams of finely divided co-crystallite powder of potassium terephthalate, rhodium chloride and potassium chloroplatinate.

20 grams of the co-crystallite powder were then dry blended with 54.06 grams of 90 percent potassium hydroxide powder and 59.89 grams of potassium carbonate powder in a Waring blender to produce 134 grams of a uniform powdered mixture. This entire powdered mixture was transferred to a rotating quartz calcining tube equipped for continuous argon purge and at ambient temperature. The quartz tube containing the powdered mixture was then placed into a tubular furnace which had been preheated to 650° C. The temperature of the contents of the tube rose at a rate of 11.1° C. per minute to 650° C. The quartz tube remained in the furnace at 650° C. for one hour, during which time the powdered mixture pyrolyzed to form a powdered pyrolysis product and after which time the tube was withdrawn from the furnace and allowed to cool to ambient temperature. The quartz tube and its contents were maintained under a blanket of argon throughout the period before introduction of the powdered mixture into the quartz tube, during the pyrolysis and during cool down of the quartz tube to ambient temperature. While still in the quartz tube under an argon blanket, the cooled pyrolysis product was suspended in water and transferred as a slurry from the tube to a beaker. After separation from the water, the pyrolysis product was repeatedly washed with water to remove potassium salts therefrom, as indicated by a pH of 7 for the resulting wash water. The resulting washed pyrolysis product was dried in a vacuum oven at 105° C. under a nitrogen blanket. The resulting dried pyrolysis product weighed 3.1 grams, had a BET surface area of 2579 square meters per gram and contained 3.5 percent of each of platinum and rhodium by weight, based on the weight of the pyrolysis product. The results of X-ray diffraction indicated that the platinum and rhodium were present predominantly as the elemental metals and in the form of a platinum-rhodium alloy containing 59 atomic percent of rhodium and 41 atomic percent of platinum. The alloy had a surface area of 1.13 square meters per gram, as determined by CO chemisorption, and 77 percent of the alloy had an average crystallite size of 95 Å, as determined by X-ray diffraction, the remainder having an average crystallite size below 35 Å, the limit of detectability for the instrument used.

EXAMPLE 7

The procedure of Example 1 was repeated with the following exceptions. Instead of the solution containing the soluble complex of chloroplatinate and the sodium salt of EDTA, a solution containing a soluble complex of silver ammonia chloride ($Ag(NH_3)_2Cl$) was formed by dissolving 3.93 grams of silver nitrate in 100 grams of water, adding potassium chloride to precipitate silver chloride, and then adding sufficient ammonium hydroxide to completely solubilize the silver chloride precipitate. Spray drying yielded 141 grams of finely divided co-crystallite of silver chloride and potassium terephthalate. The resulting dried pyrolysis product weighed 5.33 grams, had a BET surface area of 2316 square meters per gram, and contained 4.32 percent of silver by weight, based on the weight of the pyrolysis product. The silver was in the form of predominantly elemental silver. The dispersed silver had an average crystallite size of 145 Å, the remainder having an average crystallite size below 35 Å.

EXAMPLE 8

The procedure of Example 1 was employed with the following exceptions. 24.75 grams of terephthalic acid were added to a solution of 18.89 grams of potassium hydroxide in 200 grams of distilled water, slowly and with heating and stirring to form potassium terephthalate, and then 41.17 grams of potassium carbonate were dissolved in the solution. 6.16 grams of potassium dichromate were dissolved in 100 grams of water, and this solution was added to the solution of potassium terephthalate to form the solution for spray drying. 50 grams of the resulting co-crystallite powder from the spray drying step was then dry blended with 31.7 grams of 90 percent potassium hydroxide powder in the Waring blender. The resulting dry pyrolysis product weighed 5.7 grams, had a BET surface area of 1680 square meters per gram, and contained 30 percent of chromia ($Cr_2O_3$) by weight, based on the weight of the pyrolysis product. Two percent of the chromia had an average crystallite size of 80 Å, with the remainder having an average crystallite size below 35 Å.

EXAMPLE 9

32 grams of the product of Example 1 were blended with 309 grams of an acid stabilized aqueous alumina hydrosol containing 32 grams of alumina. The mixture was gelled (solidified) by the addition of a solution containing 7.7 milliliters of water and 7.7 milliliters of a 50 percent aqueous solution of ammonium hydroxide. The resulting mixture was then dried overnight in a forced air oven at 165° C. The dried solid was calcined at 483° C. for 48 hours. The resulting granulated product contained 1.84 weight percent of platinum, 48.16 weight percent of active carbon and 50 weight percent of alumina and had a particle size of 20–40 mesh (U.S. Sieve series).

EXAMPLE 10

The procedure of Example 9 was repeated using instead a blend of 7 grams of the product of Example 6 and 67.9 grams of the aqueous alumina hydrosol. The resulting granulated product contained 1.75 weight percent of platinum, 1.75 weight percent of rhodium, 46.5 weight percent of active carbon and 50 weight percent of alumina and had a particle size of 20–40 mesh (U.S. Sieve series).

EXAMPLE 11

The procedure of Example 9 was repeated using instead a blend of 24 grams of the product of Example 1 and 233 grams of the aqueous alumina hydrosol. The resulting granulated product contained 1.83 weight percent of platinum, 47.25 weight percent of active carbon and 50.00 weight percent of alumina and had a particle size of 20–40 mesh (U.S. Sieve series).

EXAMPLE 12

The procedure of Example 9 was repeated using instead a blend of 24 grams of the product of Example 8 and 233 grams of the alumina hydrosol. The resulting granulated product contained 15 weight percent of chromia, 35 weight percent of active carbon and 50 weight percent of alumina and had a particle size of 20–40 mesh (U.S. Sieve series).

EXAMPLE 13

The procedure of Example 9 was repeated using instead a blend of 9.12 grams of the product of Example 4 and 88.54 grams of the alumina hydrosol. The resulting granulated product contained 0.60 weight percent of nickel, 49.4 weight percent of active carbon and 50 weight percent of alumina and had a particle size of 20–40 mesh (U.S. Sieve series).

EXAMPLE 14

One part by weight of the product of Example 1 was mixed with 3 parts by weight of 90 percent potassium hydroxide to form a uniform powdered mixture, and the pyrolysis, water separation, wash and drying steps of Example 1 were repeated using this uniform powdered mixture as the starting material, to form a second pyrolysis product. This second pyrolysis step causes an effective increase in the concentration of platinum in the active carbon matrix to 10 weight percent, by removal of some of the carbon matrix by oxidation of the pyrolysis product of Example 1.

The procedure of Example 9 was repeated using instead a blend of 20 grams of this second pyrolysis product and 194 grams of the aqueous alumina hydrosol. The resulting granulated product contained 5 weight percent of platinum, 45 weight percent of active carbon and 50 weight percent of alumina and had a particle size of 20-40 mesh (U.S. Sieve series).

EXAMPLE 15

Active carbon containing ruthenium was obtained from Alfa Products (Thiokol-Ventron Division) of Danvers, Mass. The active carbon had a BET surface area of 1000-1100 square meters per gram. The ruthenium was present at a concentration level of 5 weight percent of the active carbon and had a surface area of 4.7 square meters per gram as determined by CO chemisorption. 37 percent of the ruthenium had a crystallite size less than 35 Å, and the remaining ruthenium had an average crystallite size of 115 Å, as determined by X-ray diffraction. A dry blend of 30 grams of the ruthenium-containing active carbon and 81 grams of 90 percent potassium hydroxide was pyrolyzed, rinsed and washed using the procedure of Example 1. The resulting dried pyrolysis product weighed 22.6 grams, had a BET surface area of 1500 square meters per gram and contained 5.2 percent of ruthenium, based on the weight of the pyrolysis product. The ruthenium had a surface area of 4 square meters per gram as determined by CO chemisorption and had an average crystallite size of 120 Å, as determined by X-ray diffraction.

EXAMPLE 16

The procedure of Example 9 was repeated using instead a blend of 6 grams of the product of Example 15 and 60 grams of the alumina hydrosol. The resulting granulated product contained 2.6 weight percent of ruthenium, calculated as the elemental metal, 47.4 weight percent of active carbon and 50 weight percent of alumina and had a particle size of 20-40 mesh (U.S. Sieve series).

EXAMPLES 17-22

The utility of the composition of the present invention as hydrocarbon conversion catalysts is illustrated in Examples 17-22. In particular, Examples 17-22 illustrate the use of compositions of this invention as catalysts for the hydrogenation of unsaturated aliphatic and aromatic hydrocarbons.

In each of Examples 17-22, a tubular reactor having a cross sectional area of 1.27 square centimeters and containing a bed of one of the catalytic compositions formed in Examples 9-14 was employed. The catalyst and bed height employed in each of Examples 17-22 are indicated in Table 2. A gaseous hydrocarbon feed was passed downward through the catalyst bed with hydrogen in Examples 17-22. The hydrocarbon feed was propylene in Examples 17-21 and benzene in Example 22. The hydrocarbon feed rate was 1.31 standard liters per hour in Examples 17-21 and 1.6 milliliters per hour in Example 22. The hydrogen feed rate ranged between 3.6 and 3.76 standard liters per hour in Examples 17-21 and was 10 standard liters per hour in Example 22. The catalyst bed temperatures in Examples 17-22 are indicated in Table 2. The pressures in the reactor were 3.51 kilograms per square centimeter in Examples 17"21 and 4.92 kilograms per square centimeter in Example 22. The degree of conversion of the hydrocarbon feeds for Examples 17-22 is given in Table 2. For Examples 17-21, the conversion is expressed as the percent of propylene converted to propane. For Example 22, the conversion is expressed as the percent of benzene converted to cyclohexane.

TABLE 2

| Example | Catalyst from Example | Catalyst Bed Height (Cm.) | Catalyst Bed Temperature (°C.) | Percent Conversion |
| --- | --- | --- | --- | --- |
| 17 | 9 | 25 | 75 | 100 |
| 18 | 10 | 13 | 65 | 100 |
| 19 | 11 | 13 | 63 | 100 |
| 20 | 12 | 13 | 69 | 100 |
| 21 | 13 | 17 | 65 | 19 |
|  |  |  | 82 | 45 |
|  |  |  | 85 | 74 |
|  |  |  | 94 | 83 |
| 22 | 14 | 13 | 32 | 100 |
|  |  |  | 35 | 100 |

The results of Examples 17-22 demonstrate the high activity and selectivity of the compositions of this invention as catalysts for hydrogen transfer reactions involving hydrocarbons.

EXAMPLE 23

The synthesis of ammonia was performed using the catalyst of Example 16 in the reactor, and using the general procedure, employed in Examples 17-22, with the following exceptions. The catalyst bed was about 10 centimeters in depth—that is, about 6.5 grams of catalyst. A stream of nitrogen and hydrogen passed downward through the catalyst bed at feedrates of 2.5 and 7.5 standard liters per hour, respectively. The pressure in the reactor was 8 kilograms per square centimeter. The hydrogen partial pressure was about 6 kilograms per square centimeter. Initially the catalyst was pre-reduced at 455°-485° C. in the stream of nitrogen and hydrogen. The temperature of the catalyst bed was then lowered to 205° C. and gradually raised. At 455° C., the production of ammonia commenced. While the temperature of the catalyst bed was held at about 483° C., product gas from the reactor was passed through a dilute sulfuric acid solution. Ammonia in the product gas stream was converted in the acid solution to ammonium sulfate, which was measured to determine the yield of ammonia. The yield of ammonia, in terms of its concentration in the product gas stream, was 1 weight percent, which is the maximum equilibrium concentration of ammonia under the conditions employed.

EXAMPLE 24

One half gram of the catalyst of Example 3 was suspended in an aqueous solution containing 0.8 weight percent of 4-carboxylbenzaldehyde in a sealed glass vessel pressurized with hydrogen to 5.25 kilograms per square centimeter. After the suspension was stirred for one hour at ambient temperature, 86 weight percent of the 4-carboxylbenzaldehyde was converted to 4-toluic acid.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. A method for hydrogenating an alkenyl, alkynyl, aryl, cyano, imino, carbonyl or carboxyl group in one or more organic compounds, comprising: contacting an aforesaid compound with hydrogen under hydrogenation conditions comprising a temperature in the range of from about ambient temperature to about 260° C. with an active carbon catalyst having a cage-like structure and a BET surface area of at least 800 square meters per gram and a bulk density of at least 0.1 gram per cubic centimeter and comprising a substantially uniform dispersion of a metal, metal-containing material, or both in a porous carbon matrix, wherein the dispersed metal and metal in the dispersed metal-containing material are each a transition metal and wherein the total concentration of dispersed metal and dispersed metal-containing material is from about 0.001 to about 30 weight percent, calculated as the elemental metal and based on the weight of the catalyst, wherein the catalyst is formed by a process comprising:

forming a uniform co-crystallite of a precursor of the metal or metal-containing material and of a carbon precursor, wherein the metal in the precursor of the metal or of the metal-containing material is a transition metal;

forming a uniform powdered mixture of the co-crystallite and inorganic solids comprising an alkali metal hydroxide;

pyrolyzing the powdered mixture in an inert atmosphere at a temperature in the range of from about 400° C. to about 980° C. to form the carbon matrix having the metal or metal-containing material substantially uniformly dispersed therein; and separating unreacted inorganic material and inorganic reaction products, other than the dispersed metal or metal-containing material, from the carbon matrix to form the catalyst.

2. The method of claim 1 wherein the metal-containing material is a metal oxide.

3. The method of claim 1 wherein the dispersed metal and metal in the dispersed metal-containing material are each platinum, palladium, rhodium, molybdenum, chromium, tungsten, iron, cobalt, nickel or copper.

4. The method of claim 1 wherein at least 60 percent of the surface of the catalyst is occupied by the cage-like structure.

5. The method of claim 1 wherein the combined space velocity for contacting one or more of the aforesaid compounds with the catalyst is from about 0.01 to about 10 of the compounds per hour per gram of the catalyst, the hydrogen is employed at a partial pressure of from about 2 to about 75 kilograms per square centimeter, and the total pressure is from about 4 to about 75 kilograms per square centimeter.

6. The method of claim 5 wherein the temperature is at least about 40° C., the combined space velocity for contacting one or more of the aforesaid compounds with the catalyst is from about 0.1 to about 8 of the compounds per hour per gram of the catalyst.

7. The method of claim 1 wherein the precursor of the dispersed metal or dispersed metal-containing material is a salt or complex of the metal or metal-containing material.

8. The method of claim 1 wherein the carbon precursor is a salt of an aromatic carboxylic acid or of a phenol.

9. The method of claim 8 wherein the carbon precursor is a salt of an aromatic carboxylic acid.

10. The method of claim 1 wherein (1) a solution both of the precursor of the metal or metal-containing material and of the carbon precursor of (2) a solution of the precursor of the metal or metal-containing material and a solution of the carbon precursor are spray-dried to form the co-crystallite.

11. The method of claim 10 wherein (1) an aqueous solution both of the precursor of the metal or metal-containing material and of the carbon precursor or (2) an aqueous solution of the precursor of the metal or metal-containing material and an aqueous solution of the carbon precursor are spray-dried to form the co-crystallite.

12. The method of claim 7 wherein the weight ratio of the co-crystallite-to-the alkali metal hydroxide in the uniform powdered mixture is in the range of from about 1:1 to about 1:5 calculated on a dry basis.

13. The method of claim 1 wherein the inorganic solids comprise potassium hydroxide or a mixture of potassium hydroxide and at least one of potassium carbonate and a potassium halide.

14. The method of claim 13 wherein at least 25 weight percent of the inorganic solids is potassium hydroxide.

15. The method of claim 13 wherein the powdered mixture is subjected to a temperature increase in the pyrolysis step at a rate of at least 35° C. per minute.

16. A method for hydrogenating an alkenyl, alkynyl, aryl, cyano, imino, carbonyl or carboxyl group in one or more organic compounds, comprising: contacting an aforesaid compound with hydrogen under hydrogenation conditions comprising a temperature in the range of from about ambient temperature to about 260° C. with an active carbon catalyst having a cage-like structure and a BET surface area of at least 800 square meters per gram and a bulk density of at least 0.1 gram per cubic centimeter and comprising a substantially uniform dispersion of a metal, metal-containing material, or both in a porous carbon matrix, wherein the dispersed metal and metal in the dispersed metal-containing material are each a transition metal and wherein the total concentration of dispersed metal and dispersed metal-containing material is from about 0.001 to about 30 weight percent, calculated as the elemental metal and based on the weight of the catalyst, wherein the catalyst is formed by a process comprising:

forming a carbon precursor which contains the metal or metal-containing material by the chemical reaction in solution of (1) a soluble carbon precursor having at least one anionic group chemically bound thereto and (2) a soluble cation or a soluble cationic complex of a transition metal;

precipitating and drying the metal-containing carbon precursor;

forming a uniform powdered mixture of the metal-containing carbon precursor and inorganic solids comprising an alkali metal hydroxide;

pyrolyzing the powdered mixture in an inert atmosphere at a temperature in the range of from about 400° C. to about 980° C. to form the carbon matrix having the metal or metal-containing material substantially uniformly dispersed therein; and separating unreacted inorganic material and inorganic reaction products, other than the dispersed metal or metal-containing material, from the carbon matrix to form the catalyst.

17. The method of claim 16, wherein the carbon precursor is a salt of an aromatic carboxylic acid or of a phenol.

18. The method of claim 17 wherein the carbon precursor is a salt of an aromatic carboxylic acid.

19. The method of claim 17 wherein the metal-containing carbon precursor is formed in aqueous solution.

20. The method of claim 16 wherein the weight ratio of the metal-containing carbon precursor-to-the alkali metal hydroxide in the uniform powdered mixture is in the range of from about 1:1 to about 1:5 calculated on a dry basis.

21. The method of claim 16 wherein the inorganic solids comprise potassium hydroxide or a mixture of potassium hydroxide and at least one of potassium carbonate and potassium chloride.

22. The method of claim 20 wherein at least 25 weight percent of the inorganic solids is potassium hydroxide.

23. The method of claim 16 wherein the powdered mixture is subjected to a temperature increase in the pyrolysis step at a rate of at least 35° C. per minute.

* * * * *

UNITED STATES PATENT OFFICE
CERTIFICATE OF CORRECTION

Patent No. 4,564,702   Dated January 14, 1986

Inventor(s) A. N. Wennerberg

It is certified that error appears in the above-identified patent and that said Letters Patent are hereby corrected as shown below:

Column 18, line 6, 17"21 should be --17-21--.

Column 20, line 26, Claim 7, should be --Claim 1--.

Column 22, line 1, Claim 17, should be --Claim 16--.

Signed and Sealed this

Twenty-fourth Day of June 1986

[SEAL]

Attest:

DONALD J. QUIGG

Attesting Officer   Commissioner of Patents and Trademarks